(12) United States Patent
Lai et al.

(10) Patent No.: US 11,351,394 B2
(45) Date of Patent: Jun. 7, 2022

(54) NEURAL PROBE INCORPORATING OPTICAL WAVEGUIDE AND METHOD OF MAKING THE SAME

(71) Applicants: Hsin-Yi Lai, Taipei (TW); You-Yin Chen, New Taipei (TW)

(72) Inventors: Hsin-Yi Lai, Taipei (TW); You-Yin Chen, New Taipei (TW)

( * ) Notice: Subject to any disclaimer, the term of this patent is extended or adjusted under 35 U.S.C. 154(b) by 933 days.

(21) Appl. No.: 16/133,809

(22) Filed: Sep. 18, 2018

(65) Prior Publication Data

US 2019/0091484 A1 Mar. 28, 2019

(30) Foreign Application Priority Data

Sep. 28, 2017 (CN) .......................... 201710901177.2

(51) Int. Cl.
| | | |
|---|---|---|
| *A61N 5/06* | (2006.01) | |
| *A61B 17/00* | (2006.01) | |
| *A61B 5/24* | (2021.01) | |
| *A61B 5/00* | (2006.01) | |

(52) U.S. Cl.
CPC .............. *A61N 5/0622* (2013.01); *A61B 5/24* (2021.01); *A61B 17/00* (2013.01); *A61N 5/0601* (2013.01); *A61B 5/0084* (2013.01); *A61B 2017/0053* (2013.01); *A61B 2562/0233* (2013.01); *A61B 2562/125* (2013.01); *A61N 2005/0612* (2013.01)

(58) Field of Classification Search
CPC ............... A61N 5/0622; A61N 5/0601; A61N 2005/0612; A61B 5/24; A61B 17/00; A61B 5/0084; A61B 2017/0053; A61B 2562/0233; A61B 2562/125; A61B 5/40
See application file for complete search history.

(56) References Cited

U.S. PATENT DOCUMENTS

| | | | | |
|---|---|---|---|---|
| 9,241,651 B2 * | 1/2016 | Fedder | ................. | G03F 7/0035 |
| 10,488,573 B2 * | 11/2019 | Gong | ................... | G02B 6/0043 |
| 2013/0131482 A1 * | 5/2013 | Fedder | ................. | B29C 41/042 |
| | | | | 264/494 |
| 2019/0086602 A1 * | 3/2019 | Gong | ....................... | G02B 6/00 |

OTHER PUBLICATIONS

Schwaerzle, M., et al. "Ultracompact optrode with integrated laser diode chips and SU-8 waveguides for optogenetic applications." 2013 IEEE 26th International Conference on Micro Electro Mechanical Systems (MEMS). IEEE, 2013. doi: 10.1109/MEMSYS.2013. 6474424. (Year: 2013).*

* cited by examiner

*Primary Examiner* — Jonathan T Kuo
(74) *Attorney, Agent, or Firm* — McClure, Qualey & Rodack, LLP

(57) ABSTRACT

The present invention provides a method for manufacturing a neural probe incorporated with an optical waveguide. The method for manufacturing a neural probe incorporated with an optical waveguide comprises the following steps. A mold-filling step, for providing a base with at least one groove formed therein. A disposing step, for disposing and overlaying a substrate having a plurality of electrode parts on the groove of the base. A combining step, for solidifying the photosensitive adhesive by a solidification process, the solidified photosensitive adhesive forming an optical waveguide and being combined with the substrate. A mold-releasing step, for removing the base from the optical waveguide and the substrate, the substrate and the optical waveguide forming a product.

9 Claims, 5 Drawing Sheets

NEURAL PROBE INCORPORATING OPTICAL WAVEGUIDE AND METHOD OF MAKING THE SAME

CROSS REFERENCE TO RELATED APPLICATIONS

This Non-provisional application claims priority under 35 U.S.C. § 119(a) on Patent Application No. 201710901177.2 filed in People's Republic of China on Sep. 28, 2017, the entire contents of which are hereby incorporated by reference.

BACKGROUND

1. Technical Field

This invention relates to a neural probe, in particular, to a neural probe incorporated with an optical waveguide and a manufacturing method thereof.

2. Description of Related Art

Concerning the neural probes of prior art, such as the implanted and flexible neural probes, they are usually applied to living bodies (such as human or animal bodies) to inspect specific locations thereof. For example, when inspecting specific locations of a brain with the neural probe, the neural probe may be implanted into the brain at a predetermined depth. Furthermore, the front end of the first face of the neural probe may have a plurality of micro electrode parts which correspond to specific zones of the brain, so as to obtain information of neural action associated with the concerned zones of the brain.

A specific gene in living bodies can be controlled by light. Therefore, being irradiated by a beam of a light source, such a specific gene may generate information of neural action in response to the stimulus from the beam of the light source. By the above mechanism, the neural probe may be implanted into specific zone(s) where such a specific gene locates, and information of neural action associated with such a specific gene may be obtained with the help of the micro electrode parts on the neural probe.

In prior art, the light source provided for irradiating the specific gene usually refers to a optical fiber, which is disposed on the second face of the neural probe opposite to the first face. In other words, the mentioned second face is opposite to the face on which micro electrode parts are disposed. Furthermore, as the neural probe is implanted into the specific zone(s), the optical fiber may introduce the beam of the light source into the specific zone(s) so as to control the specific gene.

However, optical fibers seldom have a biologically-compatible material. Furthermore, if the optical fiber is combined with the second face of the neural probe, space is usually left between the optical fiber and the second face of the neural probe. To fill the space between the optical fiber and neural probe, one may apply an adhesive material there-between, which may nevertheless increase whole thickness. Moreover, a common optical fiber usually has a large size or dimension. Such an optical fiber may hardly shrink its size or dimension to facilitate applications or meet requirements considering minimization.

In addition, the light source may be alternatively an optical waveguide. In this case, likewise, the optical waveguide is disposed on the second face of the neural probe opposite to the first face. Although the optical waveguide can be manufactured by the semiconductor process, such a process may still suffer from complicated operations, time-consuming, labor-consuming and high expenses, unfortunately. For the above reasons and if one tends to cost down, one can hardly manufacture all kinds of corresponding optical waveguides to meet various requirements. Under such a circumstance, one will unfortunately get a narrower or limited scope of information of neural action.

Accordingly, it may be therefore desirable to have a neural probe incorporated with an optical waveguide and a manufacturing method thereof. Regarding such a desired neural probe and method, corresponding optical waveguide can be rapidly obtained based on requirements. Furthermore, the optical waveguide may be directly formed on the neural probe, so that utilization and functionality can thus be enhanced.

SUMMARY OF THE INVENTION

Accordingly, the present invention provides a neural probe incorporated with an optical waveguide and a method of making the same, which can rapidly manufacture corresponding optical waveguide based on requirements, and the optical waveguide is directly formed on the substrate having electrode parts to form a neural probe. Various types of optical waveguides with different shapes can be rapidly manufactured based on requirements, the whole size of the neural probe can be reduced so as to achieve minimization. Thus, costs, man-power and time-consumption can be saved, and utilization and functionality can be also enhanced. Furthermore, due to minimization of size of the neural probe incorporated with the optical waveguide, size of the corresponding wound on living bodies can be reduced, and the loading as a whole can be therefore decreased.

According to an embodiment of the present invention, a method for manufacturing a neural probe incorporated with an optical waveguide is provided. The manufacturing method comprises the following steps. A mold-filling step, for providing a base with at least one groove formed therein and filling the groove with a photosensitive adhesive. A disposing step, for disposing and overlaying a substrate having a plurality of electrode parts on the groove of the base. A combining step, for solidifying the photosensitive adhesive by a solidification process, the solidified photosensitive adhesive forming an optical waveguide and being combined with the substrate. A mold-releasing step, for removing the base from the optical waveguide and the substrate, the substrate and the optical waveguide forming a product.

In some embodiments, the mold-filling step further comprises forming an opening on one side of the base, the opening feeding through the groove, disposing one end of a light guiding unit and/or a light emitting unit in the groove through the opening, the end of the light guiding unit and/or the light emitting unit being immersed in the photosensitive adhesive.

In some embodiments, further comprises connecting one end of the optical waveguide with a light emitting unit subsequent to the mold-releasing step.

In some embodiments, at the disposing step, a first face of the substrate overlays the groove, and the electrode parts are disposed on the first face of the substrate and correspond to the base.

In some embodiments, at the disposing step, a first face of the substrate overlays the groove, and the electrode parts are disposed on a second face of the substrate opposite to the first face.

In some embodiments, at the combining step, the solidification process comprises providing a light source to irradiate the photosensitive adhesive, so as to solidify the photosensitive adhesive to form the optical waveguide.

In some embodiments, the photosensitive adhesive is a high transparency photosensitive glue.

According to an embodiment of the present invention, a neural probe is provided. The neural probe comprises a substrate, a plurality of electrode parts and an optical waveguide. The electrode parts are respectively disposed on a first face of the substrate. Wherein, the optical waveguide is combined with the first face of the substrate or combined with a second face of the substrate opposite to the first face by means of the manufacturing method which makes the neural probe incorporated with the optical waveguide described above.

According to an embodiment of the present invention, a neural probe is provided. The neural probe comprises a substrate, a plurality of electrode parts and an optical waveguide. Wherein, the electrode parts are disposed on a first face of the substrate. The optical waveguide is disposed on the first face of the substrate or disposed on a second face of the substrate opposite to the first face, the optical waveguide is formed by a solidified photosensitive adhesive.

In some embodiments, the photosensitive adhesive is a high transparency photosensitive adhesive.

Compared with prior art, advantageous effects of the present invention refer to the following: the neural probe of the present invention can be obtained based on requirements, by means of rapidly manufacturing an optical waveguide from a base with a groove and a photosensitive adhesive. Wherein, the optical waveguide is immediately formed on a substrate having a plurality of electrode parts, together with the substrate, to form a product (i.e. a neural probe). From the above, various types or shapes of optical waveguides can be rapidly manufactured. Furthermore, whole size of the neural probe can be reduced so as to achieve minimization. Moreover, size of the corresponding wound on human or animal bodies can be also reduced so as to decrease the whole loading for human or animal bodies.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
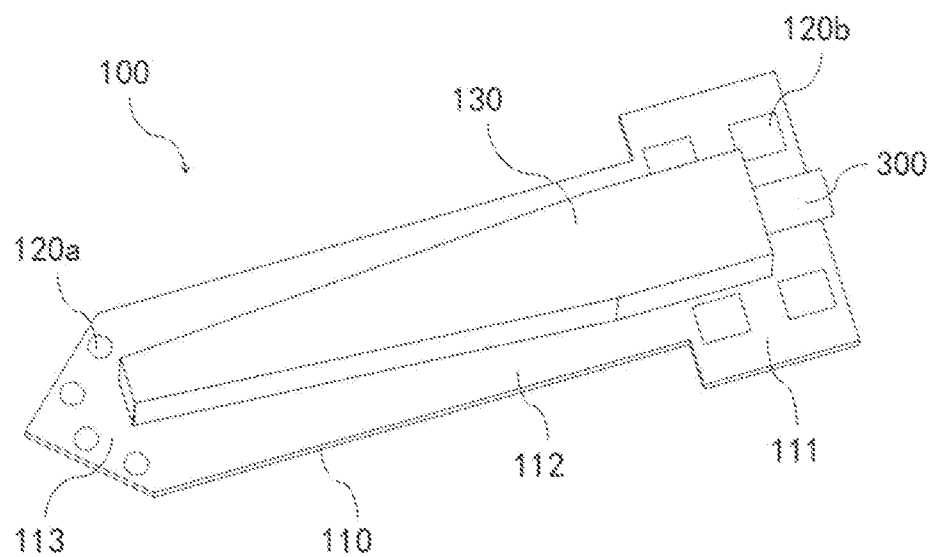
FIG. 1 is a structural schematic diagram of a neural probe according to an embodiment of the present invention.

FIG. 1 is a structural schematic diagram of a neural probe according to an embodiment of the present invention. As shown in FIG. 1, a neural probe 100 comprises a substrate 110, a plurality of electrode parts 120a and 120b, and an optical waveguide 130. The substrate 110 may have two faces opposite to each other. The electrode parts 120a and 120b may be respectively disposed on one of the two opposite faces of the substrate 110, and the optical waveguide 130 is disposed on one of the two opposite faces of the substrate 110. In other words, the electrode parts 120a and 120b may be respectively disposed on the first face of the substrate 110, and the optical waveguide 130 is disposed on the first face of the substrate 110 or on the second face of the substrate 110 opposite to the first face. The neural probe 100 of this embodiment may be but is not limited to an implanted flexible neural probe. Furthermore, the electrode parts 120a and 120b may be but are not limited to sensing probes which are utilized to sense neural electricity or obtain information of neural actions.

As shown in FIG. 1, in one embodiment, the electrode parts 120a and 120b may be respectively disposed on the first face of the substrate 110, while the optical waveguide 130 is also disposed on the first face of the substrate 110. In other words, the electrode parts 120a and 120b and the optical waveguide 130 are respectively disposed on the same face of the substrate 110.

Figure 2:
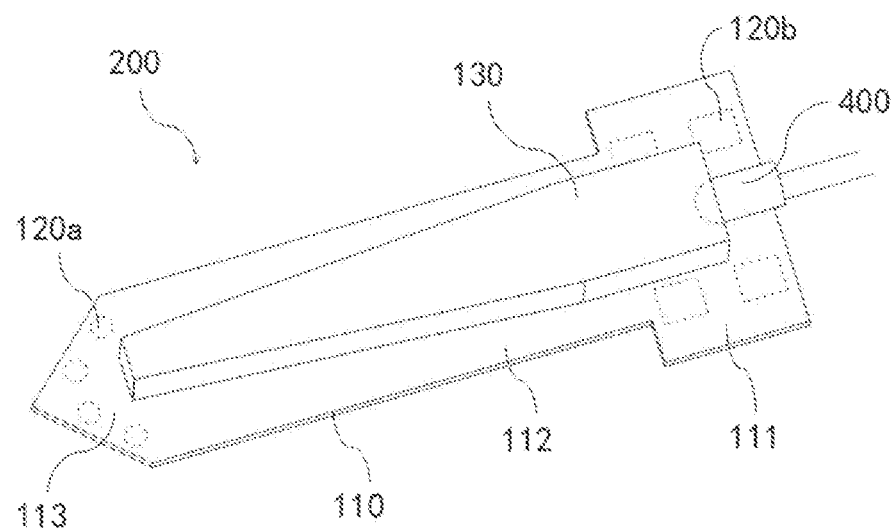
FIG. 2 is a structural schematic diagram of a neural probe according to another embodiment of the present invention.

FIG. 2 is a structural schematic diagram of a neural probe according to another embodiment of the present invention. As shown in FIGS. 1 and 2, the neural probe 200 and the electrode parts 120a and 120b thereof shown in FIG. 2 may respectively perform the same execution, operation and action as the corresponding neural probe 100 and electrode parts 120a and 120b thereof shown in FIG. 1. In FIGS. 1 and 2, the same or corresponding elements are marked with the same numerals, thus detail descriptions for the same or corresponding elements are not provided here. The major differences between the neural probe 100 in FIG. 1 and the neural probe 200 in FIG. 2 are described as follows: in FIG. 2, the neural probe 200 and the electrode parts 120a and 120b are respectively disposed on the first face of the substrate 110, while the optical waveguide 130 is disposed on the second face of the substrate 110. In other words, the electrode parts 120a and 120b and the optical waveguide 130 are respectively disposed on the two opposite faces of the substrate 110.

As shown in FIGS. 1 and 2, the substrate 110 may further include a back end 111, a middle section 112 and a needle-shaped front end 113. The middle section 112 is formed and located between the back end 111 and the needle-shaped front end 113. Furthermore, the electrode parts 120a and 120b are respectively disposed on the back end 111 and the needle-shaped front end 113 of the substrate 110. In this embodiment, the same amounts of electrode parts 120a and 120b may be respectively disposed on the back end 111 and the needle-shaped front end 113. The electrode parts 120b on the back end 111 are electrically connected to the electrode parts 120a of the needle-shaped front end 113 respectively so as to transmit signal. In addition, the electrode parts 120b on the back end 111 are further electrically connected to an external device (not shown in FIGS. 1 and 2). The external device may receive signal detected by the electrode parts 120*a* on the needle-shaped front end 113, or transmit signal to the electrode parts 120*a* on the needle-shaped front end 113.

The optical waveguide 130 of this embodiment may be incorporated with (i.e. combined with) or formed on the first face of the substrate 110. Alternatively, the optical waveguide 130 may be incorporated with (i.e. combined with) or formed on the second face of the substrate 110 opposite to the first face. The optical waveguide 130 may be further disposed or formed on a portion of the needle-shaped front end 113, the middle section 112 and the back end 111 of the substrate 110. In other words, one end of the optical waveguide 130 may be incorporated with the back end 111 of the substrate 110, while the other end of the optical waveguide 130 may be incorporated with a portion of the needle-shaped front end 113 of the substrate 110. As the optical waveguide 130 is disposed on the first face of the substrate 110, the electrode parts 120*b* on the back end 111 may surround one end of the optical waveguide 130, while the electrode parts 120*a* on the needle-shaped front end 113 may surround the other end of the optical waveguide 130. On the other hand, as the optical waveguide 130 is disposed on the second face of the substrate 110, the optical waveguide may be disposed or formed on any position of the second face of the substrate 110, which may not be limited by the electrode parts 120*a* and 120*b* of the substrate 110. The arrangement of the optical waveguide 130 described as the above is merely an example, and the present invention is not limited by the above example.

Figure 4A:
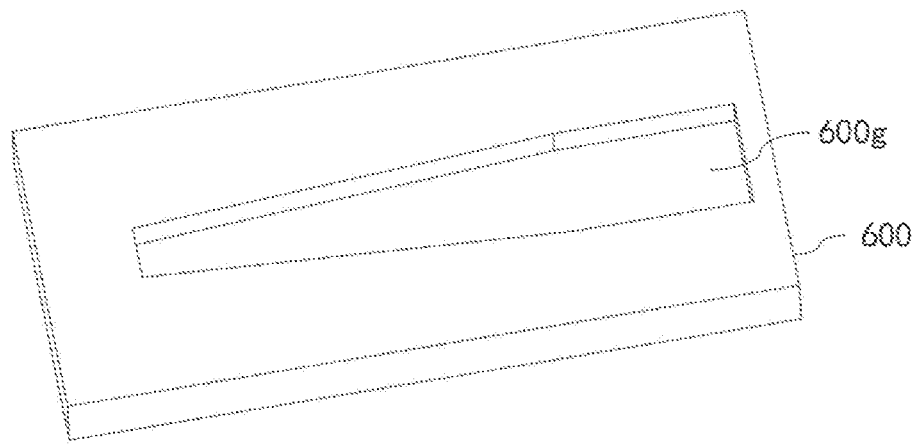
FIGS. 4A to 4E are structural schematic diagrams illustrating the process for manufacturing the neural probe incorporated with an optical waveguide according to an embodiment of the present invention.
Figure 4B:
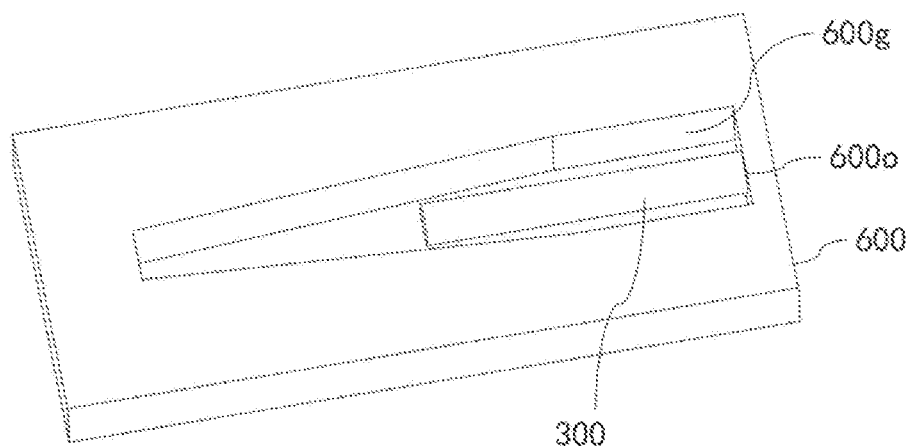
Figure 4C:
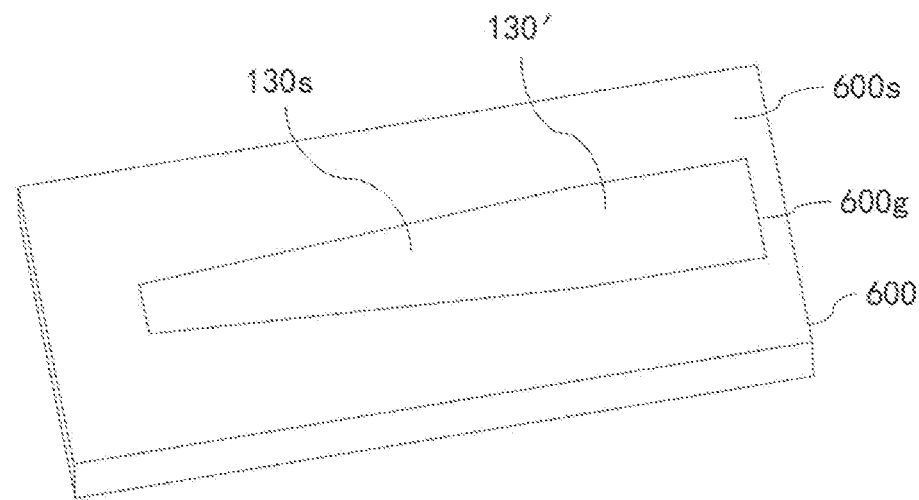

In one embodiment, the optical waveguide 130 may be formed by an solidified photosensitive adhesive 130' (as shown in FIG. 4C). The solidified photosensitive adhesive 130' may be an photosensitive glue of a biologically compatible material. Furthermore, the solidified photosensitive adhesive 130' may be a glue of a high transparency and photosensitive material which is biologically compatible, such as a ultra-violet (UV) solidified glue. In addition, the photosensitive adhesive 130' may be a liquid glue, which may then be a solidified photosensitive adhesive 130' by a solidification process. Accordingly, the solidified photosensitive adhesive 130' is of the solid state. The solidification process of this embodiment may be performed by irradiating the photosensitive adhesive 130' with a light source (not shown in FIGS. 1, 2 and 4A to 4E), and the photosensitive adhesive 130' may thus be solidified to form the optical waveguide 130. In this embodiment, the light source may be but is not limited to a ultra-violet (UV) beam.

Moreover, other differences between the neural probe 100 in FIG. 1 and the neural probe 200 in FIG. 2 are described in the following paragraphs:

The neural probe 100 in FIG. 1 may be connected to one end of a light guiding unit 300, while the neural probe 200 in FIG. 2 may be connected to one end of a light emitting unit 400.

As shown in FIG. 1, the neural probe 100 may introduce and guide a light source (not shown in FIG. 1) into the optical waveguide 130 through the light guiding unit 300. More particularly, the optical waveguide 130 may be formed or disposed on the substrate 110, and one end of the optical waveguide 130 may be connected to one end of the light guiding unit 300. In this embodiment, the light guiding unit 300 may be an optical fiber or a unit of a light guiding material.

As shown in FIG. 2, the neural probe 200 may generate and emit a light source (not shown in FIG. 2) into the optical waveguide 130 through the light emitting unit 400. More particularly, the optical waveguide 130 may be formed or disposed on the substrate 110, and one end of the optical waveguide 130 may be connected to one end of the light emitting unit 400. In this embodiment, the light emitting unit 400 may be a light-emitting diode (LED) or a unit of a light emitting material.

In another embodiment, one end of the optical waveguide 130 of the neural probe 100 may be connected to one end of the light emitting unit 400 (not shown in FIG. 2).

In another embodiment, one end of the optical waveguide 130 of the neural probe 200 in FIG. 2 may be connected to one end of the light guiding unit 300 (not shown in FIG. 2).

In another embodiment, the neural probes 100 and 200 may include a plurality of optical waveguides 130 (not shown in FIGS. 1 and 2), thus one end of the optical waveguide 130 may be respectively connected to the light emitting unit 400 and/or the light guiding unit 300.

Figure 3:
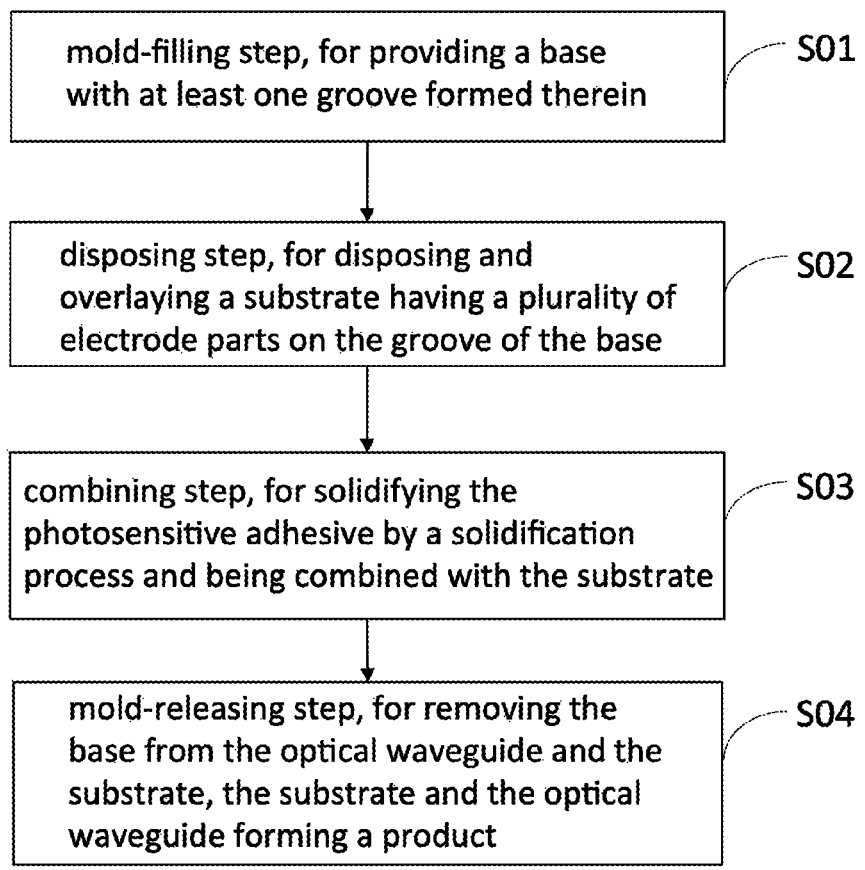
FIG. 3 is a flow diagram illustrating a method for manufacturing the neural probe incorporated with an optical waveguide according to an embodiment of the present invention.

FIG. 3 is a flow diagram illustrating a method for manufacturing the neural probe incorporated with an optical waveguide according to an embodiment of the present invention, and FIGS. 4A to 4E are structural schematic diagrams illustrating the process for manufacturing the neural probe incorporated with an optical waveguide according to an embodiment of the present invention. As shown in FIGS. 1 to 3 and 4A to 4E, the method of manufacturing a neural probe incorporated with an optical waveguide will be described as follows accompanying the flow diagram. Wherein, the steps of the flow diagram in FIG. 3 are not limited to being applied to the neural probes 100 and 200 incorporated with the optical waveguide 130 as shown in FIGS. 1, 2 and 4A to 4E. Vice versa, the neural probes 100 and 200 incorporated with the optical waveguide 130 as shown in FIGS. 1, 2 and 4A to 4E are not limited to being applied to the steps of the flow diagram in FIG. 3.

Referring to FIG. 3, in this embodiment, a substrate 110 is provided, and a plurality of electrode parts 120*a* and 120*b* are disposed on a first face of the substrate 110. Wherein, the method of manufacturing a neural probe 500 incorporated with an optical waveguide 130 comprises the following steps:

At step S01 which refers to a step of mold-filling, a base with a groove formed thereon is provided, and the groove is then filled with a photosensitive adhesive.

As shown in FIGS. 4A to 4C, at least one groove 600*g* may be formed in the base 600. In other words, the base 600 may have one or more grooves 600*g* based on requirements. If the base 600 has more than one groove 600*g*, the plurality of grooves 600*g* may feed through each other, or separated from each other, or feed through another one or others partially. When carrying out this embodiment, the base 600 and the groove 600*g* formed thereon may be designed as any types based on different requirements, and then be formed by 3D (three-dimensional) printing with a 3D-printer. Alternatively, a mold or jig of a required type suitable for the concerned base 600 and groove 600*g* may be obtained by milling and/or cutting a bulk body of rigid material with the help of laser-beam-cutting or high-pressured-water-milling. The groove 600*g* of the base 600 may exemplarily take the form of "1", "I" or "T" from a cross-sectional view or a top view. Furthermore, the groove 600*g* may exemplarily take the form of a wedge. However, the shape or form of the groove 600*g* in the present invention may have other alternatives and not be limited to the above examples. The base 600 may have a material of organic-polymer or macro molecular organic-silicon-compound such as polydimethylsiloxane (PDMS).

In one embodiment, the step of mold-filling further comprises forming an opening 600o on one side of the base 600, wherein the opening 600o may feed through the groove 600g. One end of a light guiding unit 300 and/or a light emitting unit 400 may pass through the opening 600o and thus disposed within the groove 600g. Furthermore, the end of the light guiding unit 300 and/or the light emitting unit 400 may be immersed in the photosensitive adhesive 130'. In the example where the end of the light guiding unit 300 passes through the opening 600o and is thus disposed within the groove 600g, at the step of mold-filling, an opening 600o may be formed on one side of the base 600 prior to filling the groove 600g with the photosensitive adhesive 130'. Furthermore, one or more openings 600o may be formed on the base 600 based on requirement. One end of the light guiding unit 300 may pass through the opening 600o and thus be disposed within the same groove 600g or different grooves 600g. Thereafter, the groove 600g may be filled with the photosensitive adhesive 130', so that the end of the light guiding unit 300 may be immersed in the photosensitive adhesive 130'.

In one embodiment, the photosensitive adhesive 130' may be a liquid photosensitive glue. Furthermore, as shown in FIG. 4C, the surface 130s of the filled photosensitive adhesive 130' may exemplarily extend along the same plane as the of the base 600. Alternatively, the surface 130s of the filled photosensitive adhesive 130' may exemplarily be lower than the first face 600s of the base 600 (not shown in FIG. 4C). In other words, there may be a predetermined distance between the surface 130s of the filled photosensitive adhesive 130' and the first face 600s of the base 600. However, the arrangement of the surface 130s of the filled photosensitive adhesive 130' in the present invention may have still other alternatives and not be limited to the above examples.

At step S02 which refers to a step of disposing, a substrate with a plurality of electrode parts may be disposed on and overlay the groove of the base.

Figure 4D:
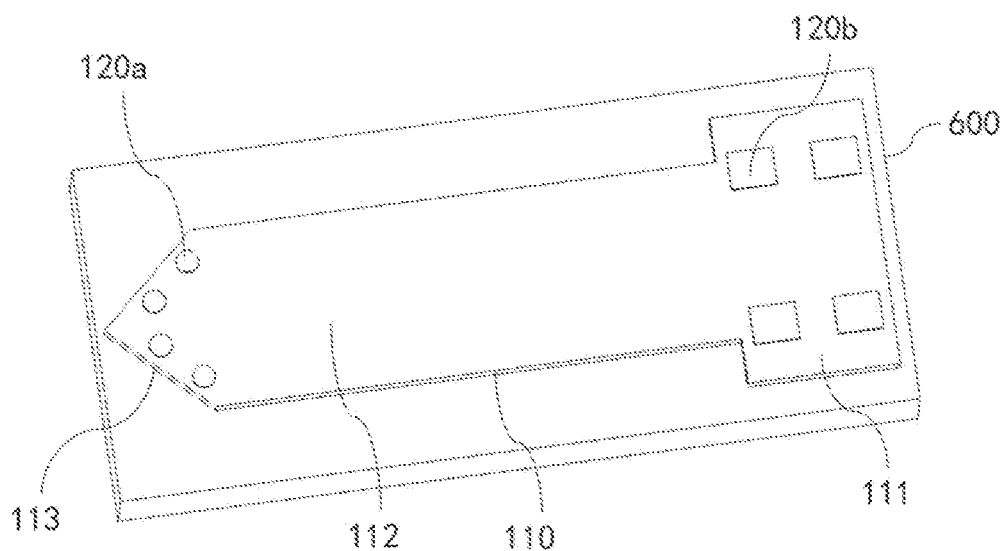

As shown in FIG. 4D, at the step of disposing, one of the two opposite faces of the substrate 110 may be disposed on and overlay the groove 600g of the base 600. In other words, the first face or second face of the substrate 110 may overlay the groove 600g of the substrate 600. Specifically, a plurality of electrode parts 120a and 120b may be disposed on the first face of the substrate 110. Accordingly, as the second face of the substrate 110 overlays the groove 600g of the base 600, the second face of the substrate 110 may correspond to the first face 600s of the base 600, while the plurality of electrode parts 120a and 120b on the first face of the substrate 110 may not correspond to the base 600.

In another embodiment, as the first face of the substrate 110 overlays the groove 600g of the base 600 (not shown in FIG. 4D), the first face of the substrate 110 may correspond to the first face 600s of the base 600, while the plurality of electrode parts 120a and 120b on the first face of the substrate 110 may correspond to the base 600. In addition, the plurality of electrode parts 120a and 120b on the substrate 110 may correspondingly surround the groove 600g (not shown in FIG. 4D).

In this embodiment, the back end 111 of the substrate 110 may be disposed adjacent to the first face 600s of the base 600 (not shown in FIG. 4D). In other words, the light guiding unit 300 and/or the light emitting unit 400 may be both disposed adjacent to the back end 111 of the substrate 110, so that light-guiding and light-emitting may be performed.

When carrying out the embodiment, the substrate 110 and the electrode parts 120a and 120b thereof shown in FIG. 4D may respectively perform the same execution, operation and action as the corresponding substrate 110 and electrode parts 120a and 120b thereof shown in FIGS. 1 and 2. Thus, detail descriptions of execution, operation and action of the substrate 110 and the electrode parts 120a and 120b in FIG. 4D are not provided here.

At step S03 which refers to a step of combining, with the help of a solidification process, the photosensitive adhesive may be solidified to form an optical waveguide and then be incorporated with (i.e. combined with) the substrate.

As shown in FIG. 4D, at the step of combining, the solidification process may comprise providing a light source (not shown in FIG. 4D) to irradiate the photosensitive adhesive 130', so that the photosensitive adhesive 130' may be solidified to form the optical waveguide. For example, as the substrate 110 is disposed on the base 600, the second face of the substrate 110 may contact the photosensitive adhesive 130'. Thereafter, the solidification process may be performed on the photosensitive adhesive 130', wherein a light source may be provided to irradiate the photosensitive adhesive 130'. As a result, the photosensitive adhesive 130' may be solidified and take a form within the groove 600g, and thus form a optical waveguide 130.

In another embodiment, the second face of the substrate 110 may not contact the photosensitive adhesive 130'. However, the photosensitive adhesive 130' may expand when being irradiated by the light source during the solidification process. Hence, after the solidification process, the expanded photosensitive adhesive 130' may still contact the substrate 110. Furthermore, the solidified photosensitive adhesive 130' may take a form within the groove 600g and thus form the optical waveguide 130.

With the help of its stickiness, the photosensitive adhesive 130' may be incorporated with (i.e. combined with) and stuck to (i.e. attached to) the substrate 110 when contacting the substrate 110. Furthermore, when radiated by the light source, the photosensitive adhesive 130' may transform from the liquid state to the solid state and thus be solidified. Such a solidified photosensitive adhesive 130' may then be firmly attached to the substrate 110. Moreover, such a solidified photosensitive adhesive 130' may form the optical waveguide 130. In this embodiment, the light source may be an ultra-violet (UV) beam.

Since the solidified photosensitive adhesive 130' (i.e. the optical waveguide 130) can be well attached to the substrate 110 with excellent adhesion, no space is left between the optical waveguide 130 and the substrate 110. Accordingly, the optical waveguide 130 can guide light well. When carrying out this embodiment, the optical waveguide 130 may be connected with a laser system (not shown in FIGS. 4D and 4E) so as to facilitate guiding of light.

Furthermore, the light guiding unit 300 and/or the light emitting unit 400 may be previously disposed in the groove 600g prior to the solidification process of the photosensitive adhesive 130'. As a result, the optical waveguide 130 formed by the solidified photosensitive adhesive 130' can be snugly connected with the light guiding unit 300 and/or the light emitting unit 400. In this manner, better optical-coupling may be achieved as the optical waveguide 130 guides light.

In this embodiment, by means of the method of manufacturing the optical waveguide 130, the required base 600 and at least one groove 600g can be rapidly and efficiently designed based on requirement. Then, filling the groove 600g with the photosensitive adhesive 130' and performing solidification process to the photosensitive adhesive 130', so as to rapidly manufacture various neural probes 500 incorporated with various types of optical waveguides 130 to meet various requirements.

At step S04 which refers to a step of mold-releasing, the base may be removed from the optical waveguide and substrate. Then, the substrate together with the optical waveguide may form a product.

Figure 4E:
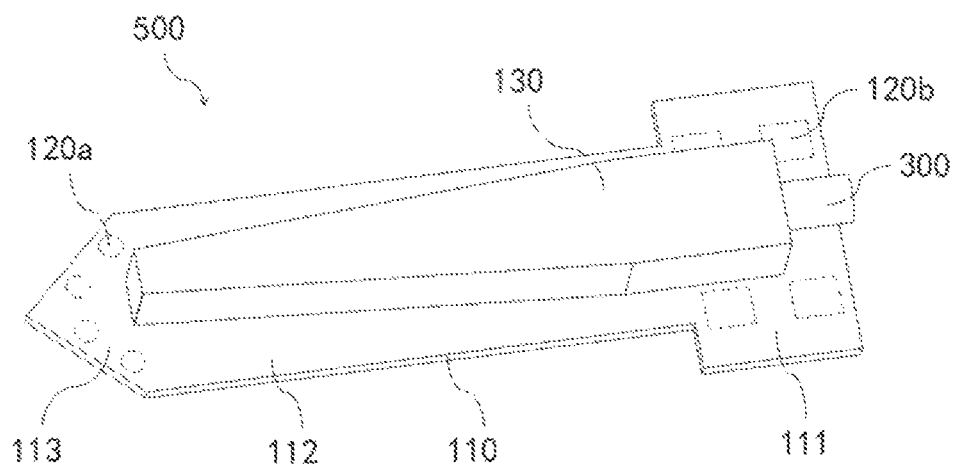

As shown in FIG. 4E, at the step of mold-releasing, with the help of well and firmly attaching between the optical waveguide 130 and the substrate 110, the optical waveguide 130 together with the substrate 110 can be easily removed from the mold (i.e. the base 600) and thus form a product. The formed product refers to a neural probe 500.

In another embodiment, as the optical waveguide 130 together with the substrate 110 form a product (i.e. form a neural probe 500), the back end 111 of the substrate 110 and one end of the optical waveguide 130 may be further connected with the light emitting unit 400 and/or the light guiding unit 300 exemplarily (not shown in FIGS. 4D and 4E). However, the present invention may still have alternative configurations which are not limited to the above example.

In summary, the optical waveguide 130 of the neural probes 100, 200 and 500 may be formed by the following steps: filling the groove 600g of the base 600 with photosensitive adhesive 130', overlaying the groove 600g of the base 600 with the substrate 110 having electrode parts 120a and 120b, and solidifying the photosensitive adhesive 130' to form an optical waveguide 130. Furthermore, the optical waveguide 130 may be attached to or combined with the substrate 110 to form the neural probes 100, 200 and 500 incorporated with the optical waveguide 130. Due to rapidity of the manufacturing process of the optical waveguide 130, and thanks that the manufactured optical waveguide 130 may be directly attached to or combined with the substrate 110 (the substrate 110 has electrode parts thereon) as the manufacturing process is done, no space will be left between the optical waveguide 130 and the substrate 110. In addition, various types of base 600 having various shapes of grooves 600g can be rapidly designed, mold-making and manufactured based on different requirements. Consequently, concerning efficiency of the manufacturing process of the base 600, the plurality of grooves 600g and the optical waveguide 130 which is immediately attached to the substrate 110, costs on time-consumption, man-power and expenses can be saved. Furthermore, the optical waveguide 130 can shrink based on different requirements, so that the neural probes 100, 200 and 500 as a whole can achieve a smaller size. Moreover, the photosensitive adhesive 130' may have a material which is biologically-compatible, thus it can be applied to living bodies. Still, due to reduced size of the neural probes 100, 200 and 500, size of the corresponding wound on living bodies can be also reduced, which can in turn decrease loading of the living bodies.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. A method for manufacturing a neural probe incorporated with an optical waveguide, the method comprising:
 a mold-filling step, for providing a base with at least one groove formed therein and filling the groove with a photosensitive adhesive;
 a disposing step, for disposing and overlaying a substrate having a plurality of electrode parts on the groove of the base;
 a combining step, for solidifying the photosensitive adhesive by a solidification process, the solidified photosensitive adhesive forming an optical waveguide and being combined with the substrate; and
 a mold-releasing step, for removing the base from the optical waveguide and the substrate, the substrate and the optical waveguide forming a product.

2. The manufacturing method of claim 1, wherein the mold-filling step further comprising:
 forming an opening on one side of the base, the opening feeding through the groove; and
 disposing one end of a light guiding unit and/or a light emitting unit in the groove through the opening, the end of the light guiding unit and/or the light emitting unit being immersed in the photosensitive adhesive.

3. The manufacturing method of claim 1, further comprising:
 connecting one end of the optical waveguide with a light emitting unit and/or a light guiding unit subsequent to the mold-releasing step.

4. The manufacturing method of claim 1, wherein at the disposing step, a first face of the substrate overlays the groove, and the electrode parts are disposed on the first face of the substrate and correspond to the base.

5. The manufacturing method of claim 1, wherein at the disposing step, a second face of the substrate overlays the groove, and the electrode parts are disposed on a first face of the substrate opposite to the second face.

6. The manufacturing method of claim 1, wherein at the combining step, the solidification process comprises providing a light source to irradiate the photosensitive adhesive, so as to solidify the photosensitive adhesive to form the optical waveguide.

7. The manufacturing method of claim 1, wherein the photosensitive adhesive is a high transparency photosensitive glue.

8. A neural probe, comprising:
 a substrate;
 a plurality of electrode parts, being respectively disposed on a first face of the substrate; and
 an optical waveguide, being combined with the first face of the substrate or combined with a second face of the substrate opposite to the first face by means of the manufacturing method of claim 1.

9. The neural probe of claim 8, wherein the photosensitive adhesive is a high transparency photosensitive adhesive.

* * * * *